United States Patent
Breard

Patent Number: 5,984,923
Date of Patent: Nov. 16, 1999

[54] ANTI-SHIFTING SYSTEM FOR SPINAL ARTHRODESIS BAR

[75] Inventor: Francis Henri Breard, Paris, France

[73] Assignee: Science et Medecine (SEM), Montrouge, France

[21] Appl. No.: 08/981,801

[22] PCT Filed: Apr. 24, 1997

[86] PCT No.: PCT/FR97/00730

§ 371 Date: Jan. 8, 1998

§ 102(e) Date: Jan. 8, 1998

[87] PCT Pub. No.: WO97/31579

PCT Pub. Date: Sep. 4, 1997

[51] Int. Cl.⁶ .................................................. A61B 17/56
[52] U.S. Cl. ......................................................... 606/61
[58] Field of Search .............................. 606/61, 62, 603, 606/71, 72, 73

[56] References Cited

U.S. PATENT DOCUMENTS 5,176,680  1/1993  Vignaud et al. ............................ 606/61
5,437,669  8/1995  Yuan et al. .
5,536,268  7/1996  Griss .......................................... 606/61
5,540,688  7/1996  Navas ........................................ 606/61

FOREIGN PATENT DOCUMENTS 0346521A  12/1989  European Pat. Off. .
0498709A   8/1992  European Pat. Off. .
0737449A  10/1996  European Pat. Off. .
9218381 U   2/1994  Germany .
9402695 U   4/1994  Germany .

Primary Examiner—Michael Buiz
Assistant Examiner—(Jackie)Tan-Uyen T. Ho
Attorney, Agent, or Firm—Collard & Roe, P.C.

[57] ABSTRACT

A system for surgically stabilizing the spine is useful for preventing shifting of the joining bars on the vertebral units of fixation. For this purpose, the joining bars are provided at predetermined intervals with anti-shifting spherical bosses having a greater diameter than each bar. Thus the anti-shifting unit is dumbbell-shaped and has a length required for the morphological features of the spine.

6 Claims, 3 Drawing Sheets

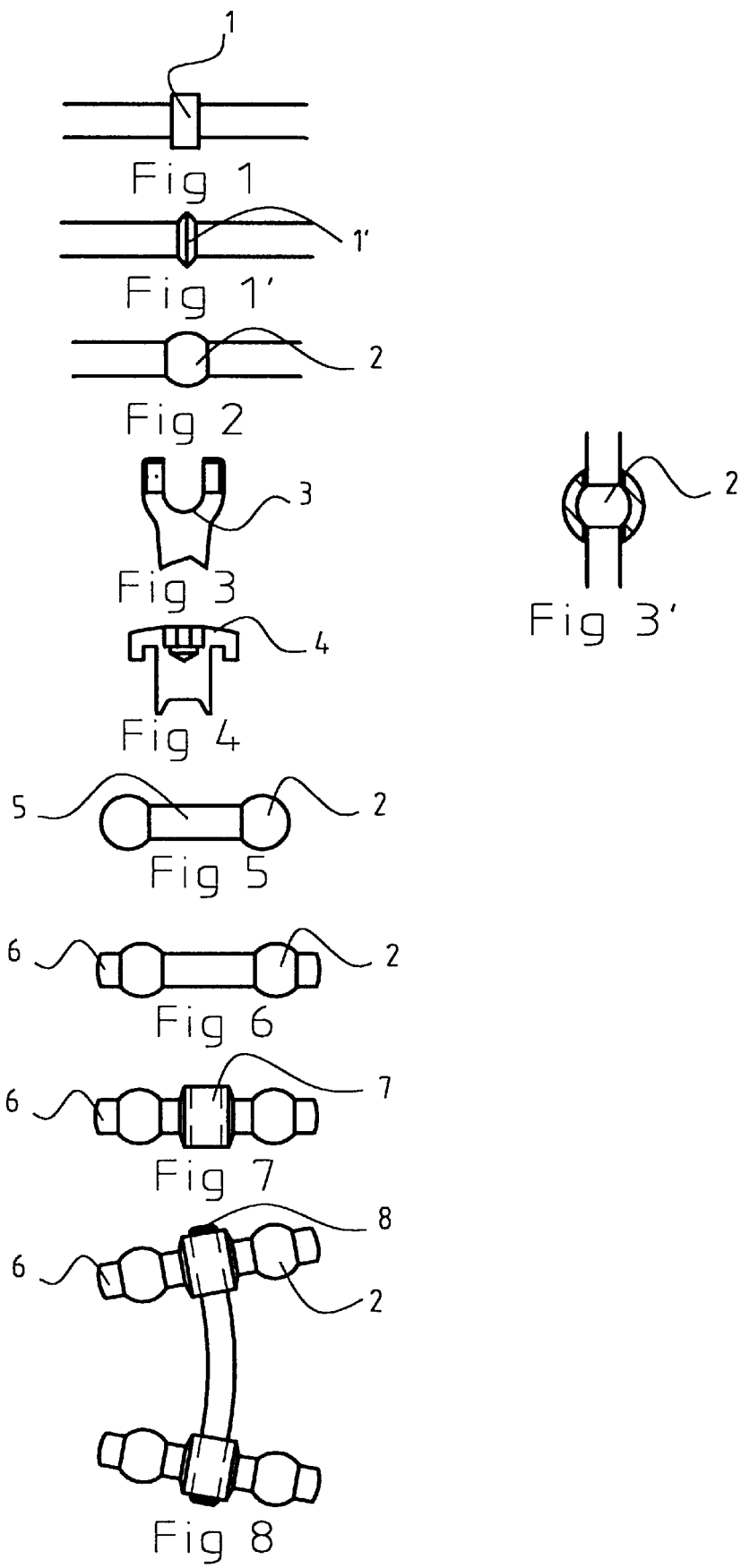

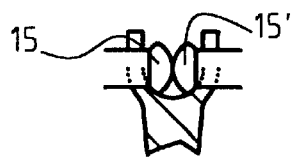
Fig 15            Fig 15'
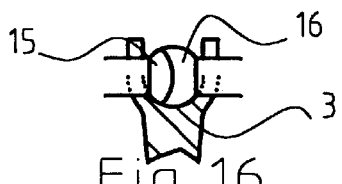
Fig 16
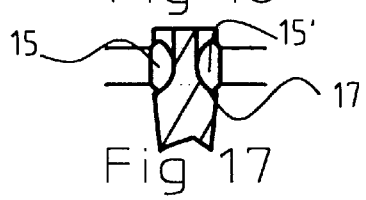
Fig 17
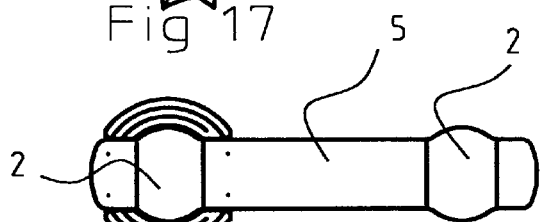
Fig 18
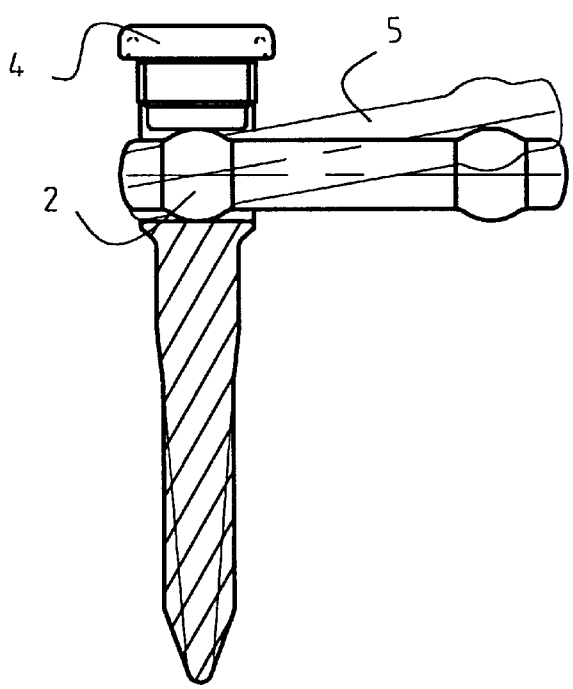
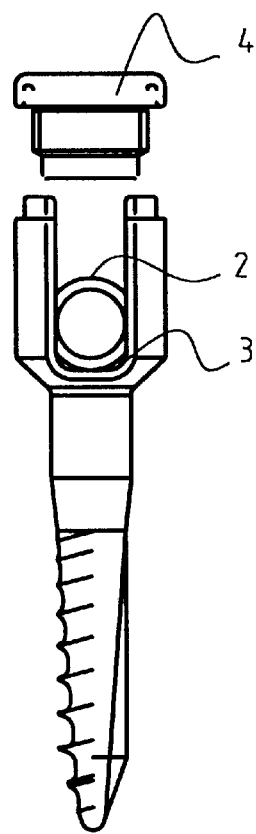
Fig 19            Fig 20

ANTI-SHIFTING SYSTEM FOR SPINAL ARTHRODESIS BAR

BACKGROUND OF THE INVENTION

1. Field of the Invention

The invention relates to the surgical stabilisation of the spine.

2. The Prior Art

The principle of stabilisation of algesic spine by means of vertebral arthrodesis has been known to orthopaedic-surgeons for many years. Arthrodesis is achieved after perfect immobilisation of the vertebrae by means of a rigid frame which acts as a support to the pathological spine. This frame is constituted of plates, or non distorsion bars, placed in situ, firmly fixed to the spine using screws or hooks.

If a bar is used, these screws include a threaded rod which is intended to be set into a vertebra, and an extra-osseous head tulip-shaped and slotted to the diameter of the said bar. The bar is bolted to the screw by means of a point screw or a vice. However, no matter how tight the point screw or the vice, the permanent stress which the spine undergoes finally causes the bar to shift in its support.

To limit this drawback, special surface structures of the bar have been suggested (serrated surface structure, cross-hatched surface structure EP 0348 272), or the use of special locking rings has been advocated (FR 83 07450/2545350). Nonetheless, about 7% of failures occur, due to the shifting of the bars in their fixing members.

SUMMARY OF THE INVENTION

It is an object of the invention to provide an anti-shifting device in which the above-mentioned drawbacks, i.e. the shifting of the linking bars on the means of fixation to the vertebrae, are avoided.

The concept of the present invention consists in increasing the diameter of the bar at defined intervals with bosses, like double-convex lenses (1') or washers (1) to be fitted inside the tulip-shaped head of the means of fixation, preventing any shifting.

BRIEF DESCRIPTION OF THE DRAWINGS

FIG. 1 shows a spinal stabilizing frame according to the invention;

FIG. 1' shows a spinal stabilizing frame with linking bars;

FIG. 2 shows a spinal stabilizing frame with an anti-shifting boss;

FIG. 3 shows a means of fixation;

FIG. 3' shows another means of fixation;

FIG. 4 shows a further means of fixation;

FIG. 5 shows a spinal stabilizing frame with spherical anti-shifting bosses;

FIG. 6 shows another embodiment with spherical anti-shifting bosses;

FIG. 7 shows another embodiment with spherical anti-shifting bosses;

FIG. 8 shows two spinal stabilizers joined together;

FIG. 15 shows two anti-shifting bosses in the form of a double-convex lens;

FIG. 15' shows the two bosses of FIG. 15 fitted into a single cavity;

FIG. 16 shows two bosses in the form of a concave sphere into which a double-convex lens is fitted;

FIG. 17 shows two linking bars with two double-convex lenses on both sides of a fixation means;

FIG. 18 shows a top view of a linking bar coupled to a fixation means;

FIG. 19 shows a front view of a linking bar coupled to a fixation means; and

FIG. 20 shows a side view of a linking bar coupled to a fixation means.

DETAILED DESCRIPTION OF PREFERRED EMBODIMENTS

Figure 9:
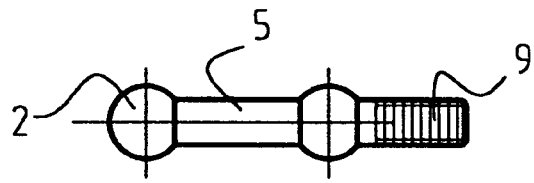
FIG. 9 shows a spinal stabilizer frame having a threaded bar at one end.
Figure 10:
FIG. 10 shows a spinal stabilizer frame having a threaded bar at two ends.
Figure 11:
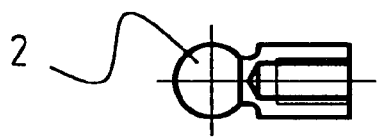
FIG. 11 shows a linking bar having a cylindrical part with cross tapping in its center.
Figure 12:
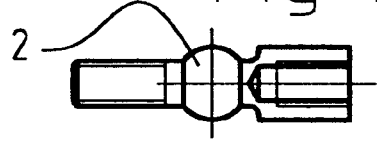
FIG. 12 shows another linking bar having a cylindrical part with cross tapping in its center.
Figure 13:
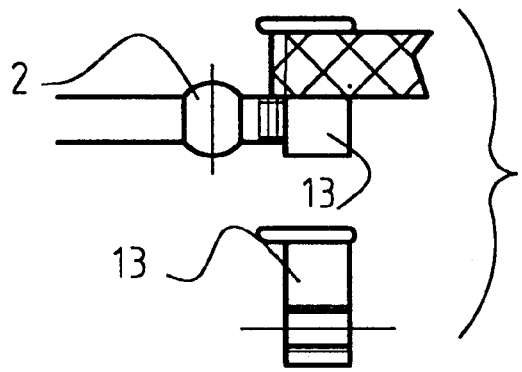
FIG. 13 shows another embodiment of a linking bar with a threaded attachment.
Figure 14:
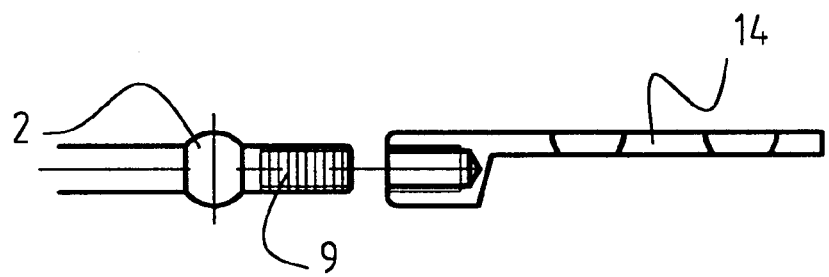
FIG. 14 shows a linking bar with a threaded end and an attachable arm.

According to a preferred embodiment, these bosses having the form of spheres (2) are integral with the linking bar and perfectly congruent with the cavity of the means of fixation (3) [profile view] and (3') [top view], these being closed by the plug (4). Thus, in its simplest form, the linking bar has the form of a small dumb-bell (5), the predefined length of which is adapted to the morphology of the spine. Different sizes are required, with spaces between the spheres ranging from 15 to 35 mm, in steps of 1 to 5 mm. A slight extension (6) of the linking bar after the sphere improves resistance to rotation. A linking bar comprising an oversized cylindrical part in the centre with a cross tapping (7) going right through it, with an equivalent diameter to the washers, lenses or spheres, doubles the safety of the compression assembly and enables a transversal threaded bar to be fitted at each extremity (8) to join together two tapped bars.

Advantageously, the linking bar has a threaded extension at one (9) or both ends (10), intended to receive a complementary piece with anti-shifting bosses, in the form of an extension consisting of a tapped bar adapted to the thread of the linking bar, and of an anti-shifting sphere (11, 12), of a ligament carrier-cylinder tapped perpendicularly to its axis (13) or of a sacral plate (14).

According to an embodiment of the invention, the anti-shifting system is in the form of a monobloc piece consisting of the dumb-bell bar and of one of the complementary pieces. As the means of fixation (3, 3') are set at an angle to the vertical, the sphere (2) is replaced either by ⅓ of a sphere or of a double-convex lens, two opposing parts (15, 15') of which may be fitted into a single cavity of said means of fixation (3, 3'), or by a sphere with a greater diameter, ⅔ of a sphere (16) hollowed out into a concavity into which ⅓ of the sphere (15, 15') of a second bar fits.

According to a further embodiment of the invention, the linking bar has two double-convex lenses positioned on both sides of a mean of fixation with solid head slotted on both faces, each with a congruent concavity (17) to the aforementioned double-convex lenses.

FIGS. 18, 19 and 20 show the type assembly with a dumb-bell bar (5) seen from above (18), in profile (19) and in alignment (20), the sphere of which fits into a tulip-shaped mean of fixation.

What is claimed is:

1. A spinal stabilizing frame comprising means of fixation (3) to spinal vertebrae and rigid linking bars (5, 6) which link said means of fixation;

each linking bar (5, 6) has anti-shifting bosses (1, 1', 2), which are oversized in relation to a diameter of the bar, each anti-shifting boss is a double-convex lens, said bosses arranged in steps of 1 to 5 mm and fit into an appropriate cavity in the means of fixation (3); and wherein anti-shifting bosses on two of said linking bars are fitted into a single cavity of said means of fixation.

2. A spinal stabilizing frame comprising means of fixation (3) to spinal vertebrae and rigid linking bars (5, 6) which link said means of fixation;

said linking bars (5, 6) have anti-shifting bosses (1, 1', 2) which are oversized in relation to a diameter of the bar, said bosses arranged in steps of 1 to 5 mm and fit into an appropriate cavity of the means of fixation (3); and wherein one anti-shifting boss is a concave sphere on one linking bar and another anti-shifting boss is a convex lens (15) on another linking bar;

wherein said concave sphere and said convex lens on said linking bars are fitted into a single cavity to form a sphere.

3. A spinal stabilizing frame comprising means of fixation (3) to spinal vertebrae and rigid linking bars (5, 6) which link a means of fixation having a plurality of cavities;

said linking bars (5, 6) have anti-shifting bosses (1, 1', 2) which are oversized in relation to a diameter of the bar, each anti-shifting boss is a double-convex lens, said bosses arranged in steps of 1 to 5 mm; and one linking bar has a double-convex lens situated in a cavity on one side of said means of fixation and another linking bar has a double-convex lens situated in a cavity on an opposite side of said means of fixation.

4. A spinal stabilizing frame comprising means of fixation (3) to spinal vertebrae and rigid linking bars (5, 6) which link said means of fixation;

said linking bars (5, 6) have anti-shifting bosses (1, 1', 2) which are oversized in relation to a diameter of the bar, said bosses arranged in steps of 1 to 5 mm and fit into an appropriate cavity of the means of fixation (3); and each of said linking bars have an oversized cylindrical part (7) in a center, with cross tapping going through the cylindrical part, which enables a transversal threaded bar to be assembled at each end of the threaded bar to join two cross tapped linking bars.

5. A spinal stabilizing frame comprising means of fixation (3) to spinal vertebrae and rigid linking bars (5, 6) which link said means of fixation;

said linking bars (5, 6) have anti-shifting bosses (1, 1', 2) which are oversized in relation to a diameter of the bar, said bosses arranged in steps of 1 to 5 mm, and fit into an appropriate cavity of the means of fixation (3); and said linking bars have a thread at one (9) end or at two ends (9) and (10) for receiving a complementary piece (11, 12, 13, 14).

6. A spinal stabilizing frame according to claim 5, wherein said complementary piece of said linking bars has anti-shifting bosses in the form of an extension comprising a tapped bar adapted to the thread of said linking bars and an anti-shifting sphere (11, 12), a ligament carrier-cylinder tapped perpendicularly to its axis (13), or a sacral plate (14).

* * * * *

UNITED STATES PATENT AND TRADEMARK OFFICE
CERTIFICATE OF CORRECTION

PATENT NO. : 5,984,923
DATED : December 27, 1999
INVENTOR(S) : FRANCIS HENRI BREARD It is certified that error appears in the above-indentified patent and that said Letters Patent is hereby corrected as shown below:

On the title page, column 1, after Item [87], please insert

--[30]    Foreign Application Priority Data

May 9, 1996    [FR]    France ............ 96/05781--

Signed and Sealed this

Twenty-fifth Day of July, 2000

Attest:

Q. TODD DICKINSON

*Attesting Officer*    *Director of Patents and Trademarks*